United States Patent
Misawa et al.

[11] Patent Number: 5,602,239
[45] Date of Patent: Feb. 11, 1997

[54] 5-O-DESOSAMINYLERYTHRONOLIDE DERIVATIVES

[75] Inventors: Yoko Misawa; Toshifumi Asaka; Masato Kashimura; Shigeo Morimoto; Katsuo Hatayama, all of Tokyo, Japan

[73] Assignee: Taisho Pharmaceutical Co., Ltd., Japan

[21] Appl. No.: 491,860

[22] PCT Filed: Jan. 24, 1994

[86] PCT No.: PCT/JP94/00087

§ 371 Date: Jul. 13, 1995

§ 102(e) Date: Jul. 13, 1995

[87] PCT Pub. No.: WO94/17088

PCT Pub. Date: Aug. 4, 1994

[30] Foreign Application Priority Data

Jan. 26, 1993 [JP] Japan .................................. 5-010351

[51] Int. Cl.⁶ .................................................. C07H 17/08
[52] U.S. Cl. ............................. 536/7.4; 536/7.1; 536/7.2; 536/7.3
[58] Field of Search ............................. 536/7.2, 7.3, 7.4, 536/7.1

[56] References Cited

U.S. PATENT DOCUMENTS 3,923,784  12/1975  Kierstead et al. ...................... 536/7.2

5,444,051  8/1995  Agouridar et al. ...................... 514/29

FOREIGN PATENT DOCUMENTS

A487411   5/1992   European Pat. Off. .
A619320  12/1992   European Pat. Off. .

*Primary Examiner*—Elli Peselev
*Attorney, Agent, or Firm*—Lorusso & Loud

[57] ABSTRACT

A novel macloride antibiotic having a potent antibacterial activity, represented by the formula:

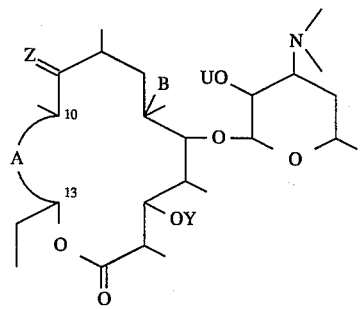

which is obtained by introducing a specific aryloxy or alkoxy group into the 3-position of a 5-O-desosaminylerythronolide derivative; or phamaceutically acceptable acid addition salts thereof.

1 Claim, No Drawings

5-O-DESOSAMINYLERYTHRONOLIDE DERIVATIVES

TECHNICAL FIELD

The present invention relates to novel derivatives of an antibacterial erythromycin, and more particularly relates to novel derivatives of 5-O-desosaminylerythronolide and pharmaceutically acceptable acid addition salts thereof.

BACKGROUND OF ART

Erythromycins are antibiotics clinically widely used as agents for treating infectious diseases caused by Gram-positive bacteria, some Gram-negative bacteria, mycoplasmas, etc. Many erythromycin derivatives have been prepared for the improvement of biological and/or pharmacological properties of erythromycins. Examples of prior art 5-O-desosaminylerythronolide derivative are 3-O-acyl-5-O-desosaminylerythronolide derivatives described in U.S. Pat. No. 3,923,784. However, prior art 5-O-desosaminylerythronolide derivatives are generally considered as inferior in the antibacterial properties, and actually, the above-mentioned derivatives have extremely weak antibacterial activity. An object of the present invention is to provide novel antibiotics having a strong antibacterial activity.

DISCLOSURE OF THE INVENTION

As a result of various researches on the antibacterial activity of novel 5-O-desosaminylerythronolide derivatives, the present inventors have found that the compounds wherein a specific aryloxy group or an alkoxy group is introduced at the 3-position of 5-O-desosaminylerythronolide derivatives have unexpectedly an extremely strong antibacterial activity, and the present invention has been accomplished.

The present invention relates to a 5-O-desosaminylerythronolide derivative represented by the formula:

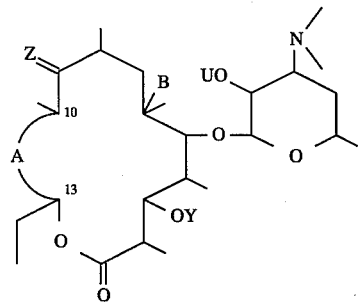

[wherein A is a group represented by the formula:

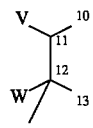

(wherein V is a hydroxyl group, W is a hydrogen atom or a hydroxyl group, or V and W together with the carbon atoms at the 11- and 12-positions form a cyclic carbonate group) or a group represented by the formula:

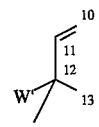

(wherein W' is a hydrogen atom or a hydroxyl group), B is a hydroxyl group or a methoxy group, U is a hydrogen atom or a $C_2$–$C_8$ alkanoyl group, Y is a $C_4$–$C_6$ cyclic alkyl group containing an oxygen atom, a phenyl group, a phenyl group substituted by one to 5 members selected from the group consisting of halogen atoms, nitro groups, trifluoromethyl groups and amino groups, a glucopyranosyl group, a ribopyranosyl group, a glucopyranosyl group substituted by an acetyl group or a benzyl group on the hydroxyl group, a ribopyranosyl group substituted by an acetyl group or a benzyl group on the hydroxyl group, a benzyl group, a benzyl group substituted by a $C_1$–$C_3$ alkyl group; or methyl group, Z is an oxygen atom or a group represented by the formula: =N-O-$R^1$ (wherein $R^1$ is a hydrogen atom, a $C_2$–$C_8$ alkanoyl group, a benzyl group or a benzyl group substituted by one to 5 members selected from the group consisting of halogen atoms and $C_1$–$C_4$ alkyl groups)] or a pharmaceutically acceptable acid addition salt thereof.

In the present invention, the alkanoyl group refers to, for example, an acetyl group, a propionyl group or benzoyl group. The cyclic alkyl group containing an oxygen atom refers to, for example, a tetrahydropyranyl group or a tetrahydrofuranyl group. The halogen atom refers to a fluorine atom, a chlorine atom, a bromine atom or an iodine atom. The alkyl group refers to a straight or branched chain alkyl group. The pharmaceutically acceptable acid addition salt refers to, for example, acetate, propionate, butyrate, formate, trifluoroacetate, maleate, tartrate, citrate, stearate, succinate, ethylsuccinate, lactobionate, gluconate, glucoheptonate, benzoate, methanesulfonate, ethanesulfonate, 2-hydroxyethanesulfonate, benzenesulfonate, p-toluenesulfonate, laurylsulfate, malate, aspartate, glutaminate, adipate, cysteine salt, hydrochloride, hydrobromide, phosphate, sulfate, hydroiodide, nicotinate, oxalate, picrate, thiocyanate, undecanoate, polyacrylate or carboxyvinyl polymer salt.

The compounds of the invention are those in which the configurations at the 3-position include both of a natural type (S-form) and a non-natural type (R-form).

The compounds of the present invention can be prepared, for example, as follows.

[Preparation Method 1] Method Using 6-O-methylerythromycin A 9-oxime as a Starting Material Step (1)

6-O-Methylerythromycin A 9-oxime is first reacted with an acid in an organic solvent at a temperature of from 0° C. to 30° C. to give a compound represented by the formula (a):

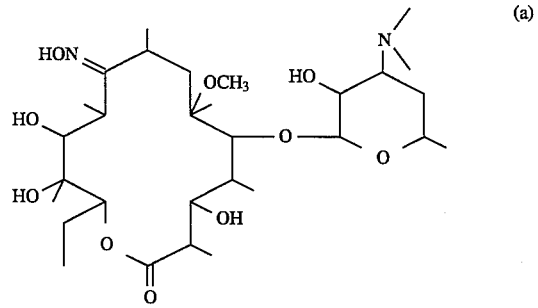

Examples of the organic solvent to be used herein are a lower alcohol (e.g. methanol, ethanol, propyl alcohol or butyl alcohol), and examples of the acid to be used are hydrochloric acid, hydrobromic acid and sulfuric acid. Preferable reaction temperature is room temperature.

Step (2)

The compound (a) is reacted with an acid anhydride represented by the formula $R^2_2O$ (wherein $R^2$ is an alkanoyl group or a benzoyl group) and a base in an inert solvent or an acid halide represented by the formula $R^3$-X (wherein $R^3$ is an alkanoyl group, a benzoyl group or a benzyloxycarbonyl group, and X is a halogen atom) and a base in an inert solvent at a temperature of from 0° C. to 30° C. to give a compound represented by the formula (b):

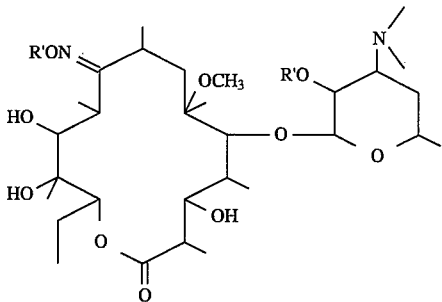
(b)

(wherein R' is the same as defined in $R^2$ or $R^3$). Examples of the inert solvent to be used herein are dichloromethane, dichloroethane, acetone and pyridine. The acid anhydride and acid halide to be used are those, for example, of acetic acid, propionic acid or benzoic acid. Examples of the base to be used are sodium bicarbonate, sodium carbonate, potassium carbonate, triethylamine, pyridine and tributylamine.

Step (3)

The compound (b) is reacted with a glucopyranosyl group or a ribopyranosyl group, each of which is substituted by an acyl group, a halogen atom, an imidate group or a 3,5-dinitropyridyl group on the 1-hydroxyl group in an inert solvent in the presence of an acid catalyst at a temperature of from −30° C. to 30° C. according to the method described in the literature [Tetrahedron Letters, Vol. 28, No. 50, page 6281 (1987)] to give a compound of the present invention represented by the formula (c):

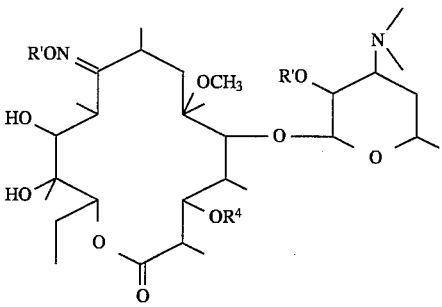
(c)

(wherein R' is as defined above, and $R^4$ is a glucopyranosyl group or a ribopyranosyl group, each of which is substituted by an acetyl group or a benzyl group on the hydroxyl group). Examples of the inert solvent to be used herein are dichloromethane, toluene, acetonitrile, ether and n-hexane, and examples of the acid catalyst to be used are boron trifluoride ether complex, copper trifluoromethanesulfonate, silver perchlorate, tin chloride and p-toluenesulfonic acid.

Step (4)

Then, the compound (c) is reacted with a base in a lower alcohol or an aqueous lower alcohol at a temperature of from room temperature to 80° C. to give a compound of the present invention represented by the formula (d):

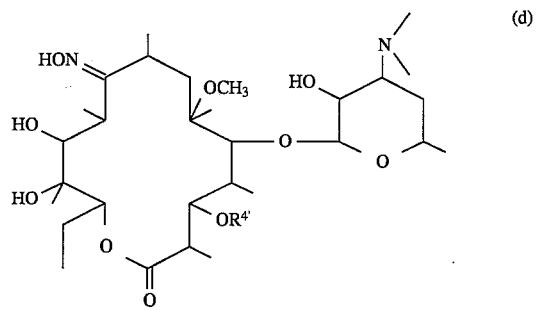
(d)

(wherein $R^{4'}$ is a glucopyranosyl group or a ribopyranosyl group). The lower alcohol to be used herein is the same as in Step (1), and the base to be used herein includes sodium bicarbonate.

Step (5)

Further, the compound (a) is reacted with an alkyl halide represented by the formula: $R^5$-X (wherein $R^5$ is a benzyl group or a benzyl group substituted by one to 5 members selected from the group consisting of halogen atoms and alkyl groups having 1 to 4 carbon atoms, and X is as defined above) and a base in an inert solvent at a temperature of from −20° C. to 30° C. to give a compound of the present invention represented by the formula (e):

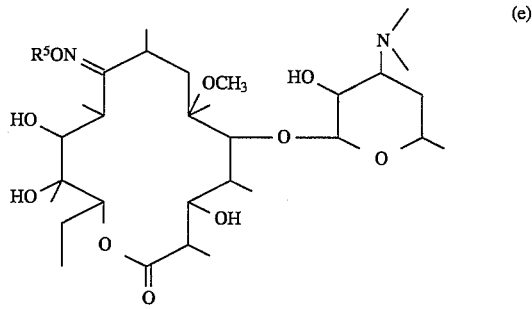
(e)

(wherein $R^5$ is as defined above). Examples of the inert solvent to be used herein are N,N-dimethylformamide, tetrahydrofuran, dimethyl sulfoxide, dioxane and a mixture thereof. Examples of the base to be used are potassium hydroxide, sodium hydroxide, sodium hydride, butyl lithium and sodium carbonate.

Step (6)

The compound of the formula (e) is reacted in the same conditions as in Step (2) to give a compound of the formula (f):

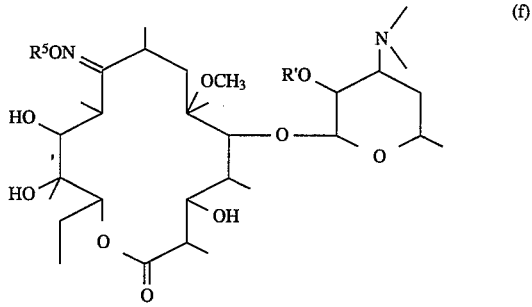
(f)

(wherein $R^5$ and R' are as defined above).

Step (7)

The compound (f) is reacted with an alkyl halide represented by the formula: $R^6$-X (wherein $R^6$ is a methyl group, a phenyl group, a benzyl group, a phenyl group substituted by one to 5 members selected from the group consisting of halogen atoms, nitro groups, trifluoromethyl groups and amino groups, or a benzyl group substituted by one to 5 members selected from the group consisting of halogen atoms, nitro groups, trifluoromethyl groups and amino groups, and X is as defined above) under the same conditions as in Step (5), followed by reaction under the same conditions as in Step (4) for removal of the protective group R' at the 2'-position to give a compound of the present invention represented by the formula (g):

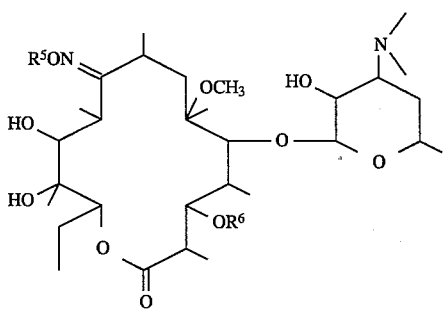
(g)

(wherein $R^5$ and $R^6$ are as defined above). The compound (g) can be also obtained by further reacting the compound (e) in the same manner as in Step (5).

Step (8)

The compound (e) is reacted with a cyclic vinyl ether containing an oxygen atom in an inert solvent in the presence of an acid catalyst at a temperature of from 0° C. to 30° C. to give a compound of the present invention represented by the formula (h):

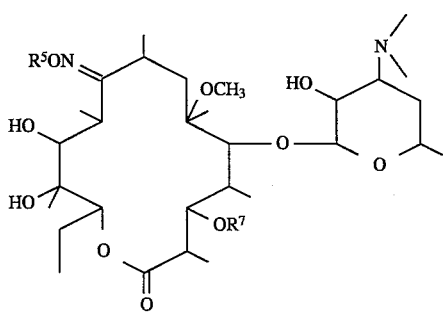
(h)

(wherein $R^5$ is as defined above and $R^7$ is a cyclic alkyl group containing an oxygen atom). The inert solvent and the acid catalyst to be used herein are the same as in Step (3).

Step (9)

Each of the compound (g) and the compound (h) is reduced in a lower alcohol in the presence of palladium as a catalyst to give a compound of the present invention represented by the formula (i):

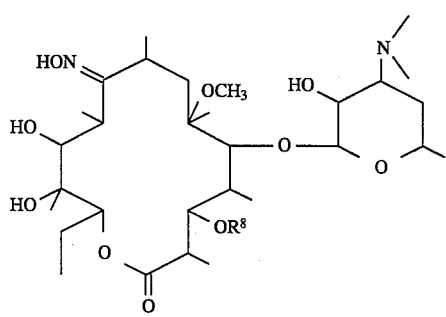
(i)

(wherein $R^8$ is the same group as defined in $R^6$ or $R^7$).

Step (10)

The compound (i) is deoximated by using sodium bisulfite, sodium nitrite or titanium trichloride in an aqueous lower alcohol at a temperature of from 0° C. to 80° C. to give a compound of the present invention represented by the formula (j):

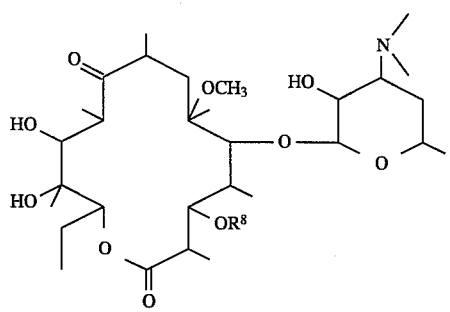
(j)

(wherein $R^8$ is as defined above).

[Preparation Method 2] Method Using 2'-O,3'-N-bis-(benzyloxycarbonyl)-N-demethyl-6-O-methylerythromycin A 9-[O-(2-chlorobenzyl)oxime] described in U.S. Pat. No. 4,680,386 as a Starting Material Step (11)

2'-O,3'-N-Bis(benzyloxycarbonyl)-N-demethyl-6-O-methylerythromycin A 9-[O-(2-chlorobenzyl)-oxime] is reacted in the same manner as in Step (1), and the resulting compound is subjected to 11,12-cyclic carbonation using a reagent such as phosgene dimer or phosgene trimer and a base such as pyridine in an inert solvent at a temperature of from −20° C. to 5° C. to give a compound represented by the formula (k):

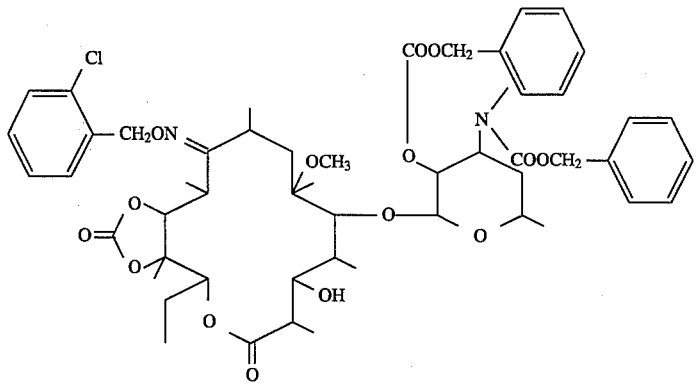
(k)

Step (12)

Then, the compound (k) is reacted in the same manner as in Step (5) to give a compound represented by the formula (l):

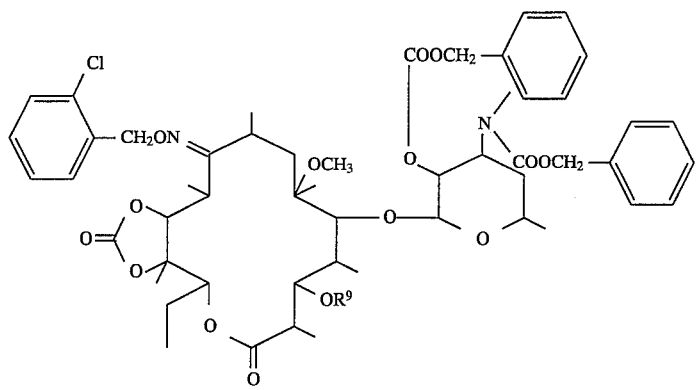

(l)

(wherein $R^9$ is a methyl group or a phenyl group which may be optionally substituted by one to 5 members selected from the group consisting of halogen atoms, nitro groups, trifluoromethyl groups and amino groups).

Step (13)

The compound (l) is reacted in the same manner as in Step (9) for reductive removal of the protective groups, and then subjected to 3'-N-methylation using formic acid or formalin to give a compound of the present invention represented by the formula (m):

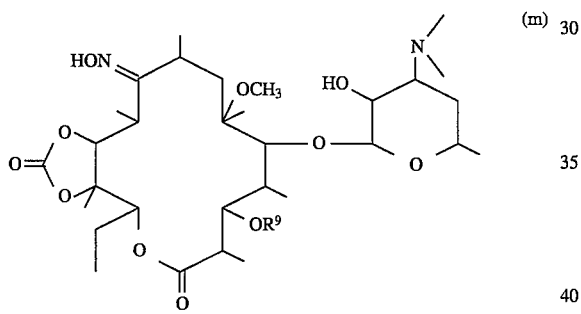

(wherein $R^9$ is as defined above).

Step (14)

The compound (m) is reacted in the same manner as in Step (10) to give a compound of the present invention represented by the formula (n):

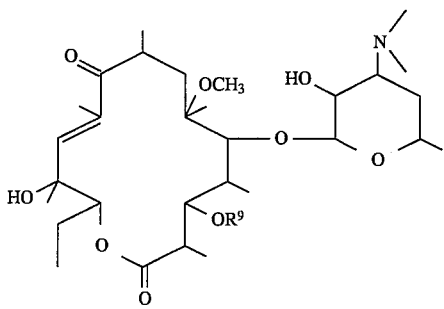

(wherein $R^9$ is as defined above).

[Preparation Method 3] Method Using 5-O-desosaminyl-6-O-methylerythronolide A as a Starting Material Step (15)

5-O-Desosaminyl-6-O-methylerythronolide A is reacted in the same manner as in Step (5) to give a compound of the present invention represented by the formula (o):

(o)

(wherein $R^9$ is as defined above).

Step (16)

5-O-Desosaminyl-6-O-methylerythronolide A is reacted in the same manner as in Step (2), and subjected to 11,12-cyclic carbonation using a reagent such as phosgene dimer or phosgene trimer and a base such as pyridine in an inert solvent at a temperature of from −20° C. to 5° C., followed by reaction in the same manner as in Step (4) to give a compound represented by the formula (p):

(p)

Step (17)

The compound (p) is reacted in the same manner as in Step (5) to give a compound of the present invention represented by the formula (q):

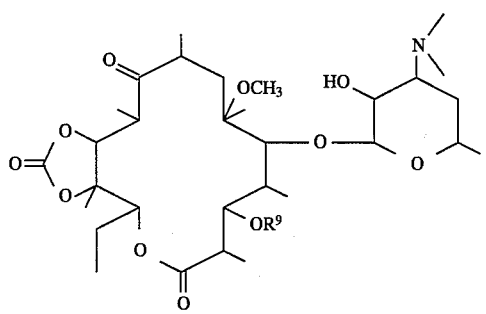

(q)

(wherein R⁹ is as defined above).
[Preparation Method 4]

The compound of the present invention can be also obtained by reacting erythromycin A 9-oxime as a starting material under the same conditions as in Preparation Method 1.

The compounds of the present invention can be administered orally or parenterally in the dosage form such as, for example, tablets, capsules, powders, troches, ointments, suspensions, suppositories and injections, all of which can be prepared by conventional preparation techniques.

Industrial Utilization

The compounds of the present invention have a strong antibacterial activity against erythromycin-sensitive bacteria and resistant bacteria. Therefore, the compounds of the present invention are useful as antibacterial agents for the treatment of infectious diseases caused by bacteria in human beings and animals (including farm animals).

Best Mode for Carrying Out the Invention

The present invention is illustrated in more detail by the following examples.

EXAMPLE 1

Preparation of
3-O-(2,4-dinitro)phenyl-5-O-desosaminyl-6-O-methylerythronolide A To a solution of 1.178 g (2 mmoles) of 5-O-desosaminyl-6-O-methylerythronolide A in 10 ml of tetrahydrofuran were added 2.5 ml (20 mmoles) of 2,4-dinitrofluorobenzene and 240 mg (6 mmoles) of 60% sodium hydride under ice-cooling. The temperature was allowed to return to room temperature gradually, the mixture was stirred for 24 hours, and the reaction solution was extracted with ethyl acetate. The ethyl acetate layer was washed with a saturated aqueous sodium chloride solution and dried over anhydrous magnesium sulfate, and then the solvent was evaporated under reduced pressure. The residue was purified by silica gel column chromatography (eluent; chloroform: methanol: 25% aqueous ammonia=95:5:0.5) to give 880 mg of the title compound as a yellow foam.

Mass (FAB) m/z; 756 [MH]⁺

¹H-NMR (200 MHz, CDCl₃) δ (ppm); 2.28(6H, s), 3.10(3H, s), 3.27(1H, s), 4.04(1H, d, J=7 Hz), 4.10(1H, s), 4.77(1H, d, J=11 Hz), 7.49, 7.53(1H), 8.43~8.50(1H), 8.66~8.69(1H)

IR(KBr, cm⁻¹); 3436, 1732, 1692, 1607, 1540, 1344, 1282, 1174

EXAMPLE 2

Preparation of
3-O-(2-nitro-4-trifluoromethyl)-phenyl-5-O-desosaminyl-6-O-methylerythronolide A To a solution of 1.178 g (2 mmoles) of 5-O-desosaminyl-6-O-methylerythronolide A in 10 ml of tetrahydrofuran were added 1.40 ml (10 mmoles) of 4-fluoro-3nitrobenzotrifluoride and 120 mg (3 mmoles) of 60% sodium hydride under ice-cooling. The temperature was allowed to return to room temperature gradually, the mixture was stirred for 5 hours and worked up in the same manner as in Example 1 to give 1.04 g of the title compound as a yellow foam.

Mass (FAB) m/z; 779 [MH]⁺

¹H-NMR (200 MHz, CDCl₃) δ (ppm); 2.31(6H, s), 3.10(3H, s), 3.26(1H, s), 4.07(1H, s), 4.74(1H, d, J=11Hz), 7.42, 7.47(1H), 7.78~7.85(1H), 8.03, 8.04(1H)

IR(KBr, cm⁻¹) ; 3436, 1732, 1693, 1626, 1543, 1327, 1282, 1175

EXAMPLE 3

Preparation of
3-O-(2-nitro)phenyl-5-O-desosaminyl-6-O-methylerythronolide A 1,178 g (2 mmoles) of 5-O-desosaminyl-6-O-methylerythronolide A was reacted with 2.1 ml (20 mmoles) of 2-nitrofluorobenzene, 280 mg (7 mmoles) of 60% sodium hydride and 15 ml of tetrahydrofuran in the same manner as in Example 1 to give 560 mg of the title compound as a yellow foam.

Mass (FAB) m/z; 711 [MH]⁺

¹H-NMR (200 MHz, CDCl₃) δ (ppm); 2.26(6H, s), 3.11(3H, s), 4.07(1H, s), 4.11(1H, d, J=7 Hz), 4.68(1H, d, J=11Hz), 6.97~7.05(1H), 7.27~7.33(1H), 7.49~7.57(1H), 7.72~7.77(1H)

IR(KBr, cm⁻¹); 3467, 1732, 1692, 1605, 1530, 1276, 1173

EXAMPLE 4

Preparation of
3-O-(4-methyl-2-nitro)phenyl-5-O-desosaminyl-6-O-methylerythronolide A 1.178 g (2 mmoles) of 5-O-desosaminyl-6-O-methylerythronolide A was reacted with 3.10 g (20 mmoles) of 4-fluoro-3-nitrotoluene, 200 mg (5 mmoles) of 60% sodium hydride and 10 ml of tetrahydrofuran in the same manner as in Example 1 to give 460 mg of the title compound as a yellow foam.

Mass (FAB) m/z; 725 [MH]⁺

¹H-NMR (200MHZ, CDCl₃) δ (ppm); 2.28(6H, s), 2.34(3H, s), 3.10(3H, s), 3.25( 1H, broad-s), 4.05(1H, s), 4.13(1H, d, J=7 Hz), 4.62(1H, d, J=11 Hz), 7.15, 7.20(1H), 7.29~7.35( 1H), 7.54, 7.55(1H)

IR(KBr, cm⁻¹) ; 3459, 1731, 1692, 1533, 1258, 1173

EXAMPLE 5

Preparation of
3-O-(4-fluoro-2-nitro)phenyl-5-O-desosaminyl-6-O-methylerythronolide A One gram (1.698 mmoles) of 5-O-desosaminyl-6-O-methylerythronolide A was reacted with 0.92 ml (8.49 mmoles) of 2,5-difluoronitrobenzene, 152 mg (3.80 mmoles) of 60% sodium hydride and 10 ml of tetrahydrofuran in the same manner as in Example 1 to give 387 mg of the title compound as a yellow foam.

Mass (FAB) m/z: 729 [MH]+

$^1$H-NMR (200 MHz, CDCl$_3$) δ (ppm) ; 2.38(6H, s), 3.10(3H, s), 3.26(1H, s), 4.05(1H, s), 4.13(1H, d, J=7 Hz), 4.60(1H, d, J=11 Hz ), 7.17~7.31(2H), 7.49~7.56(1H)

IR(KBr, cm$^{-1}$) ; 3467, 1732, 1692, 1538, 1265, 1174

EXAMPLE 6

Preparation of
3-O-(4,5-difluoro-2-nitro)phenyl-5-O-desosaminyl-6-O-methylerythronolide A One gram (1.698 mmoles) of 5-O-desosaminyl-6-O-methylerythronolide A was reacted with 0.98 ml (8.49 mmoles) of 2,4,5-trifluoronitrobenzene, 102 mg (2.547 mmoles) of 60% sodium hydride and 10 ml of tetrahydrofuran in the same manner as in Example 1 to give 87 mg of the title compound as a yellow powder.

Mass (FAB) m/z; 747 [MH]+

$^1$H-NMR (200 MHz, CDCl$_3$) δ (ppm); 2.28(6H, s), 3.09(3H, s), 4.06(1H, d, J=7 Hz), 4.50(1H, d, J=11 Hz), 7.12~7.23(1H), 7.73~7.83(1H)

IR(KBr, cm$^{-1}$); 3460, 1732, 1693, 1540, 1333, 1174

EXAMPLE 7

Preparation of
3-O-(2,3-difluoro-6-nitro)phenyl-5-O-desosaminyl-6-O-methylerythronolide A One gram (1.698 mmoles) of 5-O-desosaminyl-6-O-methylerythronolide A was reacted with 0.99 ml (8.49 mmoles) of 2,3,4-trifluoronitrobenzene, 102 mg (2.547 mmoles) of 60% sodium hydride and 10 ml of tetrahydrofuran in the same manner as in Example 1 to give 820 mg of the title compound as a yellow foam.

Mass (FAB) m/z; 747 [MH]+

$^1$H-NMR (200 MHz, CDCl$_3$) δ (ppm): 2.26(6H, s), 3.07(3H, s), 3.25(1H, broad-s), 4.00(1H, s), 4.19(1H, d, J=7 Hz), 5.00(1H, d, J=11 Hz), 6.85~6.98(1H), 7.53~7.63(1H)

IR(KBr, cm$^{-1}$); 3467, 1734, 1540, 1467, 1173

EXAMPLE 8

Preparation of
3-O-(2-amino)phenyl-5-O-desosaminyl-6-O-methylerythronolide A

To a solution of 500 mg (0.704 mmole) of the compound obtained in Example 3 in 5 ml of methanol were added 335 mg (1.41 mmoles) of nickel chloride hexahydrate and 107 mg (2.816 mmoles) of sodium borohydride under ice-cooling. After stirring for 1.5 hours, the reaction solution was poured into aqueous ammonia, followed by extraction with ethyl acetate. Purification in the same manner as in Example 1 gave 230 mg of the title compound as a pale brown foam.

Mass (FAB) m/z; 681 [MH]+

$^1$H-NMR (200 MHz, CDCl$_3$) δ (ppm); 2.25(6H, s), 3.10(3H, s), 4.00(1H, s), 4.55(1H, d, J=11 Hz), 6.65~7.03(4H)

IR(KBr, cm$^{-1}$) ; 3452, 1732, 1692, 1504, 1459, 1172

EXAMPLE 9

Preparation of
3-O-(2,4-dinitro)phenyl-5-O-desosaminyl-6-O-methylerythronolide A 11,12-cyclic carbonate (1) To a solution of 11.78 g (0.02 mole) of 5-O-desosaminyl-6-O-methylerythronolide A in 100 ml of acetone was added 2.27 ml (0.024 mole) of acetic anhydride under ice-cooling, followed by stirring at room temperature for 6 hours. The acetone was evaporated under reduced pressure, and the residue was extracted with dichloromethane. The dichloromethane layer was washed with a saturated aqueous sodium bicarbonate solution and a saturated aqueous sodium chloride solution successively, and dried over anhydrous magnesium sulfate. The solvent was evaporated under reduced pressure, and the residue was recrystallized from ether-n-hexane to give 12.17 g of 2'-O-acetyl-5-O-desosaminyl-6-O-methylerythronolide A as a white powder.

mp; 158°~160° C.

Mass (FAB) m/z; 632 [MH]+

$^1$H-NMR (200 MHz, CDCl$_3$) δ (ppm); 2.07(3H, s), 2.26(6H, s), 2.95(3H, s), 3.26(1H, s), 3.96(1H, s)

IR(KBr, cm$^{-1}$); 3469, 1750, 1733, 1693

(2) To a solution of 50 g (84.8 mmoles) of the compound obtained in the above (1) in 500 ml of dichloromethane was added 102.6 ml (1.27 moles) of pyridine under ice-cooling, and then a solution of 25.4 ml (212 mmoles) of trichloromethyl chloroformate in 40 ml of dichloromethane was added dropwise thereto at the same temperature, followed by stirring for 5.5 hours. Cooled water and a saturated aqueous sodium bicarbonate solution were added gradually to the reaction solution, followed by extraction with dichloromethane. The dichloromethane layer was washed with a saturated aqueous sodium bicarbonate solution and a saturated aqueous sodium chloride solution successively, and dried over anhydrous magnesium sulfate. After evaporation of the solvent under reduced pressure, the residue was purified by silica gel column chromatography (eluent; acetone: n-hexane: triethylamine=6 to 10:10:0.2) to give 41.93 g of 2'-O-acetyl-5-O-desosaminyl-6-O-methylerythronolide A 11,12-cyclic carbonate as a white foam.

$^1$H-NMR (200 MHz, CDCl$_3$) δ (ppm); 2.05(3H, s), 2.25(6H, s), 2.92(3H, s), 4.57(1H, d, J=9 Hz), 4.74(1H, s), 4.75(1H, dd, J=10 Hz, 9 Hz), 5.13(1H, dd, J=12 Hz, 2 Hz)

(3) 800 mg (1.218 mmoles) of the compound obtained in the above (2) in 5 ml of methanol was heated under reflux for 5 hours. After evaporation of the methanol, the residue was extracted with ethyl acetate. The ethyl acetate layer was washed with a saturated aqueous sodium chloride solution, and dried over anhydrous magnesium sulfate. After evaporation of the solvent under reduced pressure, the residue was recrystallized from methanol to give 603 mg of 5-O-desosaminyl-6-O-methylerythronolide A 11,12-cyclic carbonate as a white powder.

$^1$H-NMR (200 MHz, CDCl$_3$) δ (ppm); 1.51(3H, s), 2.50(6H, s), 2.94(3H, s), 4.51(1H, d, J=7 Hz), 4.76(1H, s), 5.14(1H, dd, J=11 Hz, 3 Hz)

(4) 440 mg (0.715 mmole) of the compound obtained in the above (3) was reacted with 0.6 ml (4,769 mmoles) of 2,4-dinitrofluorobenzene, 86 mg (2,145 mmoles) of 60% sodium hydride and 3 ml of tetrahydrofuran in the same manner as in Example 1 to give 300 mg of the title compound as a yellow powder.

Mass (FAB) m/z; 782 [MH]+

¹H-NMR (200 MHz, CDCl₃) δ (ppm); 1.52(3H, s), 2.42(6H, s), 3.06(3H, s), 4.06(1H, d, J=7 Hz), 4.70(1H, s), 4.80(1H, d, J=11 Hz), 7.53, 7.60(1H), 8.45~8.53(1H), 8.68, 8.70(1H)

IR(KBr, cm⁻¹); 3436, 1809, 1737, 1713, 1606, 1537, 1344, 1317, 1281

EXAMPLE 10

Preparation of 3-O-(2-methyl)benzyl-5-O-desosaminyl-6-O-methylerythronolide A 9-[O-(2chlorobenzyl)oxime]

(1) To 500 g (0.655 mole) of 6-O-methylerythromycin A 9-oxime was added 1 L of 1N hydrochloric acid, followed by allowing to stand at room temperature for 24 hours. The mixture was adjusted to pH 10 by adding sodium hydroxide solution, and the precipitated crystals were collected by filtration. The crystals were dissolved in dichloromethane, washed with a saturated aqueous sodium chloride solution and dried over anhydrous magnesium sulfate. The dichloromethane was evaporated under reduced pressure, and the residue was crystallized from methanol to give 259.8 g of 5-O-desosaminyl- 6-O-methylerythronolide A 9-oxime as white crystals.

mp; 257°~260° C.

Mass (FAB) m/z; 605 [MH]⁺

¹H-NMR (300 MHz, CDCl₃) δ (ppm); 1.42(3H, s), 2.34(6H, s), 2.99(3H, s), 3.26(1H, s), 3.57(1H, s), 4.37(1H, s), 4.42(1H, d, J=7 Hz), 5.23(1H, dd, J=11 Hz, 2 Hz), 7.43(1H, broad-s)

IR(KBr, cm⁻¹) ; 3523, 3370, 1712, 1188, 1169, 1085

Alternatively, 5-O-desosaminyl-6-O-methylerythronolide A 9-oxime was also obtained by oximation of 5-O-desosaminyl-6-O-methylerythronolide A in methanol using hydroxylamine hydrochloride and imidazole.

(2) To a solution of 3.02 g (5 mmoles) of the compound obtained in the above (1) in 30 ml of N,N-dimethylformamide were added 0.94 ml (7.50 mmoles) of 2-chlorobenzyl chloride and 240 mg (6 mmoles) of 60% sodium hydride under ice-cooling. After stirring for 5 hours, the mixture was extracted and purified in the same manners as in Example 1 to give 1.91 g of 5-O-desosaminyl-6-O-methylerythronolide A 9-[O-(2-chlorobenzyl)oxime] as a white foam.

(3) 2.148 g (2.947 mmoles) of the compound obtained in the above (2), 1.17 ml (8.841 mmoles) of 2-methyl-benzyl chloride, 525 mg (8.841 mmoles) of 96% potassium hydroxide powder and 20 ml of tetrahydrofuran were reacted in the same manner as in Example 1 to give 613 mg of the title compound as a white foam.

Mass (FAB) m/z; 833 [MH]⁺

¹H-NMR (200 MHz, CDCl₃) δ (ppm); 2.17(6H, s), 2.38(3H, s), 2.93(3H, s), 3.26(1H, s), 4.21(1H, d, J=7 Hz), 4.40(1H, s), 4.03, 4.93(2H, ABq, J=14 Hz), 5.13, 5.17(2H), 7.10~7.67(8H)

IR(KBr, cm⁻¹) ; 3447, 1732, 1457, 1170, 1083

EXAMPLE 11

Preparation of 5-O-desosaminyl-3,6-di-O-methylerythronolide A 9-oxime 11,12-cyclic carbonate (1) 5.0 g (4.38 mmoles) of 2'-O,3'-N-bis(benzyloxy-carbonyl)-N-demethyl-6-O-methylerythromycin A 9-[O-(2chlorobenzyl)oxime]was reacted in the same manner as in Example 10(1) to give 2.99 g of 2'-O,3'-N-bis(benzyloxycarbonyl)-N-demethyl-5-O-desosaminyl-6-O-methylerythronolide A 9-[O-(2-chlorobenzyl)oxime].

(2) 3.01 g (3.06 mmoles) of the compound obtained in the above (1) was reacted with 1.1 ml (9.18 mmoles) of trichloromethyl chloroformate and 4.94 ml (61.2 mmoles) of pyridine in 55 ml of dichloromethane in the same manner as in Example 9(2) to give 930 mg of 2'-O,3'-N-bis(benzyloxycarbonyl)-N-demethyl-5-O-desosaminyl-6-O-methylerythronolide A 9-[O-(2-chlorobenzyl)oxime]11,12-cyclic carbonate as a white foam.

(3) To a solution of 920 mg (0.912 mmole) of the compound obtained in the above (2) in a mixture of 7 ml of dimethyl sulfoxide and 7 ml of tetrahydrofuran were added 0.57 ml (9.12 mmoles) of methyl iodide and 110 mg (1.879 mmoles) of 96% potassium hydroxide powder under ice-cooling. The temperature was allowed to return to room temperature gradually, and the mixture was stirred for 5.5 hours. The reaction solution, after addition of 2 ml of triethylamine, was extracted with ethyl acetate, and worked up in a conventional manner. The residue was purified by silica gel column chromatography (eluent; ethyl acetate: n-hexane=1:3) to give 790 mg of 2'-O,3'-N-bis(benzyloxycarbonyl)-N-demethyl-5-O-desosaminyl-3,6-di-O-methylerythronolide A 9-[O-(2chlorobenzyl)oxime] 11,12-cyclic carbonate as a white foam.

(4) 780 mg (0.762 mmole) of the compound obtained in the above (3), 300 mg of 10% palladium carbon, 0.46 ml (12.192 mmoles) of formic acid and 96 mg (1.524 mmoles) of ammonium formate in 40 ml of methanol were together heated under reflux for 4 hours. After addition of 35% aqueous formalin solution, the mixture was heated under reflux for 3 hours, and the catalyst was removed by filtration. The methanol was evaporated under reduced pressure, and the residue was made basic with a saturated aqueous sodium carbonate solution and extracted with ethyl acetate. After working up in a conventional manner, purification by silica gel column chromatography (eluent; chloroform: methanol: 25% aqueous ammonia=20:1:0.1) gave 326 mg of the title compound as a white foam.

Mass (FAB)m/z; 645 [MH]⁺

¹H-NMR (200 MHz, CDCl₃) δ (ppm); 2.42(6H, s), 3.01(3H, s), 3.57(3H, s), 4.43(1H, d, J=8 Hz), 4.86(1H, s), 8.35(1H, broad-s)

EXAMPLE 12

Preparation of 3-O-(2-tetrahydropyranyl)-5-O-desosaminyl-6-O-methylerythronolide A (1) 2 g (2.93 mmoles) of 5-O-desosaminyl-6-O-methylerythronolide A 9-[(O-benzyl)oxime] obtained by the same reaction as in Example 10(2) using the compound obtained in Example 10(1) and benzyl chloride was dissolved in 20 ml of dichloromethane, and then 4 g of Molecular Sieves 4A, 0.84 ml (9.21 mmoles) of dihydropyrane and 892 mg (4.69 mmoles) of p-toluenesulfonic acid monohydrate were added thereto, followed by stirring at room temperature for 7 hours. The reaction solution was extracted with dichloromethane and worked up in a conventional manner. The residue was purified by silica gel column chromatography (eluent; acetone: n-hexane: triethylamine=3:10:0.2) to give 0.24 g of 3-O-(2-tetra-hydropyranyl)-5-O-desosaminyl-6-O-methylerythronolide A 9-[O-(benzyl)oxime].

(2) To a solution of 0.3 g (0.39 mmole) of the compound obtained in the above (1) in 3 ml of methanol were added 100 mg of 10% palladium carbon, 40 mg (0.63 mmole) of ammonium formate and 0.12 ml (3.13 mmoles) of 99% formic acid, followed by reaction at 50° C. for 30 minutes. After removal of the catalyst by filtration, evaporation of the solvent under reduced pressure gave 244 mg of 3-O-(2-tetrahydropyranyl)-5-O-desosaminyl-6-O-methylerythronolide A 9-oxime.

(3) To a solution of 220 mg (0.32 mmole) of the compound obtained in the above (2) in a mixture of 1 ml of ethanol and 1.5 ml of water were added 432 mg (4.15 mmoles) of sodium bisulfite and 0.02 ml (0.52 mmole) of 99% formic acid, followed by heating under reflux for 30 minutes. The mixture was made basic with 2N sodium hydroxide solution and extracted with ethyl acetate, and the solvent was evaporated under reduced pressure. The residue was purified by silica gel column chromatography (eluent; chloroform: methanol: 25% aqueous ammonia=20:1:0.1) to give 130 mg of the title compound.

Mass (FAB) m/z; 674 [MH]$^+$ $^1$H-NMR (200 MHz, CDCl$_3$) δ (ppm); 2.31(6H, s), 2.98(3H, s), 4.00(1H, m)

EXAMPLE 13

Preparation of
10,11-anhydro-5-O-desosaminyl-3,6-di-O-methylerythronolide A 280 mg (0.434 mmole) of the compound obtained in Example 11, 316 mg (3.038 mmoles) of sodium bisulfite, 5 ml of ethanol and 5 ml of water were together heated under reflux for 4 hours. Working up in the same manner as in Example 12(3) gave 66 mg of the title compound as a white foam.

Mass (FAB)m/z; 586 [MH]$^+$ $^1$H-NMR (200 MHz, CDC$_3$) δ (ppm); 2.01(3H, s), 2.31(6H, s), 3.16(3H, s), 3.56(3H, s), 4.38(1H, d, J=7 Hz), 6.45(1H, s)

EXAMPLE 14

Preparation of
5-O-desosaminyl-3,6-di-O-methylerythronolide A
9-[O-(2-chlorobenzyl)oxime]

(1) To a solution of 2.148 g (2.946 mmoles) of the compound obtained in Example 10(2) in 20 ml of dichloromethane were added 1.26 g (14.73 mmoles) of sodium bisulfite and 0.85 ml (5.892 mmoles) of benzyloxycarbonyl chloride under ice-cooling. The temperature was allowed to return to room temperature gradually, and the mixture was stirred at room temperature for 24 hours. The reaction solution was extracted with dichloromethane, and worked up in a conventional manner. The residue was purified by silica gel column chromatography (eluent; chloroform: acetone=2:1) to give 1.76 g of 2'-O-benzyloxycarbonyl-5-O-desosaminyl-6-O-methylerythronolide A 9-[O-(2-chlorobenzyl)oxime] as a white foam.

(2) 1.76 g (2.039 mmoles) of the compound obtained in the above (1) was reacted with 0.38 ml (6.117 mmoles) of methyl iodide and 357 mg (6.117 mmoles) of 96% potassium hydroxide powder in a mixture of 10 ml of dimethyl sulfoxide and 10 ml of tetrahydrofuran in the same manner as in Example 11(3) to give 550 mg of 2'-O-benzyloxycarbonyl-5-O-desosaminyl- 3,6-di-O-methylerythronolide A 9-[O-(2-chlorobenzyl)oxime] as a white foam.

(3) 150 mg (0.171 mmole) of the compound obtained in the above (2), 70 mg (0.833 mmole) of sodium bicarbonate, 13 ml of methanol and 5 ml of water were together stirred at 55° C. for 4 hours. The methanol was evaporated under reduced pressure, and the residue was extracted with ethyl acetate and worked up in a conventional manner to give 136 mg of the title compound as a white foam.

Mass (FAB) m/z; 743 [MH]$^+$ $^1$H-NMR (200 MHz, CDCl$_3$) δ (ppm); 2.32(6H, s), 2.90(3H, s), 3.56(3H, s), 4.79(2H, s), 7.15–7.49(4H)

EXAMPLE 15

Preparation of
3-O-(β-D-glucopyranosyl)-5-O-desosaminyl-6-O-methylerythronolide A 9-oxime (1) 10 g (25.6 mmoles) of α-D-glucose pentaacetate and 2 g (21.7 mmoles) of hydrazine acetate in N,N-dimethylformamide were together stirred at 50° C. for 45 minutes. The reaction solution was extracted with ethyl acetate, and washed with a saturated aqueous sodium chloride solution. After working up in a conventional manner, purification by silica gel column chromatography (eluent; ether: n-hexane =2:1 to 3:1) gave 5.45 g of 2,3,4,6-tetra-O-acetyl-α-D-glucose.

(2) To a solution of 5.45 g (15.66 mmoles) of the compound obtained in the above (1) in 15 ml of dichloromethane were added 5.45 ml (53.95 mmoles) of trichloroacetonitrile and 623 mg (15.58 mmoles) of 60% sodium hydride under ice-cooling, followed by stirring for 4 hours. The reaction solution was extracted with dichloromethane, and worked up in a conventional manner. The residue was purified by silica gel column chromatography (eluent; ether: n-hexane=3:1) to give 3.91 g of O-(2,3,4,6-tetra-O-acetyl-α-D-glucopyranosyl)-trichloroacetoimidate.

(3) To a solution of 6 g (9.936 mmoles) of the compound obtained in Example 10(1) in 240 ml of dichloromethane were added 2.32 ml (24.84 mmoles) of acetic anhydride and 4.16 g (49.68 mmoles) of sodium bicarbonate under ice-cooling. The temperature was allowed to return to room temperature gradually, and the mixture was stirred for 6.5 hours. The reaction solution was extracted with dichloromethane and worked up in a conventional manner to give 7.18 g of 2'-O-acetyl-5-O-desosaminyl-6-O-methylerythronolide A 9-acetoxime.

(4) To a solution of 1.36 g (2 mmoles) of the compound obtained in the above (3) in 15 ml of tetrahydrofuran were added 4 g of Molecular Sieves 4A, 0.3 ml (2.4 mmoles) of boron trifluoride ethyl ether complex and 1.33 g (2.7 mmoles) of the compound obtained in the above (2) under ice-cooling, followed by stirring for 7 hours. The molecular sieves were removed by filtration, the reaction solution was made basic with a saturated aqueous sodium bicarbonate solution and extracted with ethyl acetate. Working up in a conventional manner gave 680 mg of 3-O-tetraacetylglucosyl-5-O-desosaminyl-6-O-methylerythronolide A 9-acetoxime.

(5) 670 mg (6.58 mmoles) of the compound obtained in the above (4) and 0.66 ml (3.19 mmoles) of 28% sodium methoxide methanol solution were together stirred in 12 ml of methanol for 2 days. The methanol was evaporated under reduced pressure, and the residue was made basic with aqueous ammonia and extracted with ethyl acetate. After working up in a conventional manner, purification by silica gel column chromatography (eluent; chloroform: methanol= 1:1) gave 130 mg of the title compound.

Mass (FAB) m/z; 767 [MH]$^+$ $^1$H-NMR (200 MHz, CDCl$_3$) δ (ppm); 2.35(6H, s), 3.03(3H, s), 4.01(1H, s), 4.41(1H, s), 4.69(1H, s), 5.64(1H)

EXAMPLE 16

Preparation of 2'-O-acetyl-3-O-[β-D-(2,3,4-triacetyl)ribopyranosyl]-5-O-desosaminyl-6-O-methylerythronolide A 9-acetoxime 688 mg (1 mmole) of 2'-O-acetyl-5-O-desosaminyl-6-O-methylerythronolide A 9-acetoxime and 470 mg (1.12 mmoles) of a compound obtained by treating β-D-ribopyranose 1,2,3,4-tetraacetate in the same manners as in Example 15(1) and (2), were reacted in the same manner as in Example 15(4) to give 120 mg of the title compound.

$^1$H-NMR (200 MHz, CDCl$_3$) δ (ppm); 2.05(3H, s), 2.06(6H, s), 2.15(3H, s), 2.17(3H, s), 2.29(6H, s), 2.95(3H, s), 4.41(1H, d, J=8 Hz)

Experiment (In Vitro Antibacterial Activity)

The in vitro antibacterial activity of the compound of the present invention obtained in Example 9 against various experimental bacteria was measured using sensitive disc media (produced by Eiken Chemical Co.) according to the MIC measuring method specified by the Japan Society of Chemotherapy. 6-O-Methylerythromycin A was used as a comparative drug. The results are expressed as MIC value (Minimum Inhibitory Concentration, mcg/ml), and shown in Table 1.

TABLE 1

| | In vitro antibacterial activity MIC value (mcg/ml) | |
|---|---|---|
| | Compound | |
| Microorganism | Example 9 | Comparative drug |
| S. aureus 209P-JC | 0.10 | 0.10 |
| S. aureus Smith 4 | 0.10 | 0.10 |
| S. epidermides IID 866 | 0.10 | 0.10 |
| E. faecalis CSJ 1212 | 0.20 | 0.78 |
| S. aureus B1 | 0.78 | >100 |

We claim:

1. A 5-O-desosaminylerythronolide derivative represented by the formula:

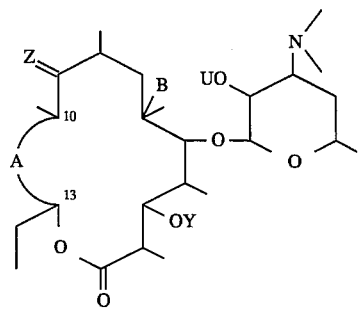

wherein A is a group represented by the formula:

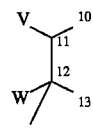

(wherein V is a hydroxyl group, W is a hydrogen atom or a hydroxyl group, or V and W together with the carbon atoms at the 11- and 12-positions form a cyclic carbonate group) or a group represented by the formula:

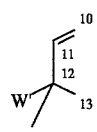

(wherein W' is a hydrogen atom or a hydroxyl group), B is a hydroxyl group or a methoxy group, U is a hydrogen atom or a C$_2$–C$_8$ alkanoyl group, Y is a tetrahydropyranyl group, a tetrahydrofuranyl group, a phenyl group, a phenyl group substituted by one to 5 members selected from the group consisting of halogen atoms, nitro groups, trifluoromethyl groups and amino groups, a glucopyranosyl group, a ribopyranosyl group, a glucopyranosyl group substituted by an acetyl group or a benzyl group on the hydroxyl group, a ribopyranosyl group substituted by an acetyl group or a benzyl group on the hydroxyl group, a benzyl group, a benzyl group substituted by a C$_1$–C$_3$ alkyl group; or methyl group, Z is an oxygen atom or a group represented by the formula: =N-O-R$^1$ (wherein R$^1$ is a hydrogen atom, a C$_2$–C$_8$ alkanoyl group, a benzyl group or a benzyl group substituted by one to 5 members selected from the group consisting of halogen atoms and C$_1$–C$_4$ alkyl groups) or a pharmaceutically acceptable acid addition salt thereof.

* * * * *

UNITED STATES PATENT AND TRADEMARK OFFICE
CERTIFICATE OF CORRECTION

PATENT NO. : 5,602,239
DATED : February 11, 1997
INVENTOR(S) : MISAWA et al

It is certified that error appears in the above-identified patent and that said Letters Patent is hereby corrected as shown below:

Col. 12, line 62, "4,769" should read --4.769--; and line 63, "2,145" should read --2.145--.

Col. 13, line 67, "2chlorobenzyl" should read --2-chlorobenzyl--.

Col. 14, line 25, "2chlorobenzyl" should read --2-chlorobenzyl--.

Signed and Sealed this

Seventeenth Day of March, 1998

Attest:

BRUCE LEHMAN

Attesting Officer

Commissioner of Patents and Trademarks